(12) United States Patent
Greene

(10) Patent No.: US 11,957,928 B1
(45) Date of Patent: Apr. 16, 2024

(54) FRICTION-BASED THERAPEUTIC LIGHT PENILE DEVICE

(71) Applicant: Joel Greene, Flagstaff, AZ (US)

(72) Inventor: Joel Greene, Flagstaff, AZ (US)

(73) Assignee: Flow State IP LLC, Sheridan, WY (US)

( * ) Notice: Subject to any disclaimer, the term of this patent is extended or adjusted under 35 U.S.C. 154(b) by 0 days.

(21) Appl. No.: 17/961,579

(22) Filed: Oct. 7, 2022

Related U.S. Application Data (60) Provisional application No. 63/254,529, filed on Oct. 11, 2021.

(51) Int. Cl.
*A61N 5/06* (2006.01)

(52) U.S. Cl.
CPC ........ *A61N 5/06* (2013.01); *A61N 2005/0645* (2013.01); *A61N 2005/0658* (2013.01); *A61N 2005/0666* (2013.01)

(58) Field of Classification Search
CPC .............. A61N 5/06; A61N 2005/0645; A61N 2005/0658; A61N 2005/0666
See application file for complete search history.

(56) References Cited

U.S. PATENT DOCUMENTS

| | | | |
|---|---|---|---|
| 6,443,978 B1 | 3/2002 | Zharov | |
| 8,608,644 B1 | 12/2013 | Davig | |
| 9,889,314 B2 | 2/2018 | Kim et al. | |
| 10,130,550 B2 | 11/2018 | Zipper | |
| 10,537,491 B2 | 1/2020 | Courtion et al. | |
| 10,940,080 B2 | 3/2021 | Zipper | |
| 11,110,295 B1 | 9/2021 | Truckai et al. | |
| 2007/0027411 A1 | 2/2007 | Ella et al. | |
| 2009/0093856 A1 | 4/2009 | Attila et al. | |
| 2014/0200399 A1 | 7/2014 | Vandaele | |
| 2019/0038501 A1 | 2/2019 | Courtion et al. | |
| 2020/0261305 A1* | 8/2020 | Lewis | A61H 19/32 |
| 2021/0212888 A1 | 7/2021 | Zipper | |
| 2021/0299464 A1* | 9/2021 | Reign | A61N 5/0613 |
| 2022/0143420 A1 | 5/2022 | Truckai et al. | |

FOREIGN PATENT DOCUMENTS

CN 112546453 A * 3/2021 ........... A61N 5/0613

* cited by examiner

*Primary Examiner* — Ahmed M Farah
*Assistant Examiner* — Naveed R. Kolia
(74) *Attorney, Agent, or Firm* — Invention To Patent Services; Alex Hobson (57) ABSTRACT

A friction-based therapeutic light penile device is configured to provide light therapy to the penis when in an erect state to more effectively ensure penetration of the emitted therapeutic light into the penis as the skin tissue is thinner. The device forms a sleeve for insertion of the erect penis and a friction material for arousal to maintain the erection during therapy. The light devices may be configured proximal to an outer rigid shell and emit light through an elastomeric friction material. The light devices may be configured to heat the friction material for further arousal and a vibratory device may further enhance arousal. The therapeutic light may be a specific wavelength of light, such as a blue, red and/or infrared. A testicular flange may extend from the sleeve and have light devices for the scrotum and testicles. The elastomeric material may form an insertion flange that is vagina shaped.

14 Claims, 7 Drawing Sheets

| Color | Wavelength | Frequency | Photon Energy |
|---|---|---|---|
| Violet | 380–450 nm | 670–790 THz | 2.75–3.26 eV |
| Blue | 450–485 nm | 620–670 THz | 2.56–2.75 eV |
| Cyan | 485–500 nm | 600–620 THz | 2.48–2.56 eV |
| Green | 500–565 nm | 530–600 THz | 2.19–2.48 eV |
| Yellow | 565–590 nm | 510–530 THz | 2.10–2.19 eV |
| Orange | 590–625 nm | 480–510 THz | 1.98–2.10 eV |
| Red | 625–700 nm | 400–480 THz | 1.65–1.98 eV |

FRICTION-BASED THERAPEUTIC LIGHT PENILE DEVICE

CROSS REFERENCE TO RELATED APPLICATION

This application claims the benefit of U.S. provisional application No. 63/254,529, filed on Oct. 11, 2021; the entirety of which is incorporated by reference herein.

BACKGROUND OF THE INVENTION

Field of the Invention

The invention relates to a friction-based therapeutic light penile device having a sleeve for insertion of the penis therein and one or more therapeutic light devices configured to emit an emitted light onto the penis while in the sleeve and wherein the light infrared light, and/or is blue and/or red wavelength and preferably a red wavelength light, or light having a wavelength from about 625 nm to 700 nm.

Background

Erectile dysfunction has gained awareness in recent years with the introduction of medications to increase blood flow to the penis to ameliorate this condition. Men can experience a loss of genital health and tone from decreased blood flow and declining vascularization with age. Men can experience erectile dysfunction especially with age. Loss of blood flow, poor circulation, decreased levels of nitric oxide (NO), and atherosclerosis are contributing factors to erectile dysfunction (Reference 2, Reference 3, Reference 5). Taking the aforesaid medications can cause a drop in blood pressure that is unsafe for some men, especially those on blood pressure medication. In addition, these medications have to be taken in advance and this is often times hard to plan for. Many men would prefer not to have to take these medications and would appreciate remedies that were not pharmaceutical based.

SUMMARY OF THE INVENTION

The invention is directed to a friction-based therapeutic light penile device that includes a sleeve for insertion of the erect penis for light therapy therein. The sleeve is lined in the interior with a friction sleeve that provides friction for arousal to keep the penis erect during the light therapy. A plurality of light devices are configured to emit light into the sleeve and onto the erect penis. The lights may be blue and/or red wavelength light as these specific wavelengths may provide particular therapeutic benefits. The light devices may emit light through the friction material, which may be an elastomeric material that disperses the light to produce greater coverage of light incident on the penis. The sleeve may have an outer shell configured around the friction sleeve and the therapeutic light devices may be configured inside or outside of this outer shell. The outer shell may be light translucent or transparent to allow the emitted light from the therapeutic light devices to pass through the outer shell.

In addition, the sleeve may have a scrotum flange that extends orthogonally from the hollow channel of the sleeve and have one or more light devices for emitting a therapeutic light onto the scrotum, to increase blood flow function to the scrotum. The light devices may emit infrared (IR) light to warm the friction material for further arousal to maintain an erect penis during the light therapy. The friction-based therapeutic light penile device may also have a vibratory device that vibrates the light penile device for further arousal.

A friction-based therapeutic light penile device may be used to treat erectile dysfunction and/or for therapy to prevent erectile dysfunction. The sleeve may have an outer shell that is rigid, such as a hard plastic cylindrical sleeve. A friction material may form a friction sleeve that lines the interior of the rigid outer shell to form a hollow channel having an insertion opening on one end for insertion of the penis. The friction material may be elastomeric material, such as silicone or urethane, for example, and the friction material may have an index of refraction to disperse the light from the light devices. The elastomeric friction material may deform around the penis upon insertion and provide adequate friction to maintain an erect penis during the therapy.

The light devices may be coupled with the outer shell and may emit light through the friction material and into the hollow channel. The light devices may be attached to the outer shell and therefore be configured an offset distance from the inside surface of the friction sleeve. This offset distance and the dispersion characteristics may effectively spread the light emitted from the light device over an enlarge area along the inside surface of the friction sleeve to substantially cover the inside surface of the friction sleeve. This configuration may provide therapeutic light fully around the erect penis inserted into the hollow channel. In addition, the light devices being configured along the outer shell results in less stress on the light devices, as they are offset from the friction material that may be an elastic material that moves, compresses and expands during use.

A plurality of light devices may be configured along the length of the sleeve and also a circumferential offset angle from each other to provide emitted light that substantially cover the inside surface of the friction sleeve. For example, a first row of lights may be configured along the length of the sleeve and a second row of lights may be configured a circumferential offset angle around the sleeve.

In an exemplary embodiment, the light devices are configured radially outward from the outer shell or in part radially outward from the inside surface of the outer shell and emit light through an aperture in the outer shell, or have only the light producing portion of the light device protruding through an aperture in the outer shell. Also, the outer shell may be light transparent or translucent to allow the light devices to project light through the outer shell and then through the friction sleeve onto a penis and/or into the hollow channel.

The light devices may be configured with a waterproof seal from the hollow channel. The waterproof seal may be formed at least in part by the friction material. The friction material may be silicone or urethane elastomeric material which may form a seal when it is configured as a contiguous cylindrical sleeve which in the outer shell. The lights devices may also be configured behind a waterproof seal material configured along the inside surface of the outer shell, such as a film or coating of a waterproof seal material.

A sleeve of a friction-based therapeutic light penile device sleeve may have an extended end opening, configured on the opposing end of the sleeve from the insertion opening. The extended end opening may be used for cleaning the device by running water and/or cleaning solution through the hollow channel. The extended end of the outer shell, may be dome shaped around the friction sleeve.

The friction material may extend out from the outer shell on the insertion opening end to from an insertion flange for comfort during therapy. Again, the device may have a scrotum flange configured with a light device or devices to emit light onto the scrotum during therapy. The insertion flange may extend down along the testicular flange. The insertion flange may be configured to resemble a vagina for visual stimulation to aid in the achievement of an erection and maintaining an erection during the light therapy. Elastomeric material of the insertion flange may from an elongated crease between opposing sides forming the insertion opening. An elongated crease has a length that is at least five times more than a width and in an exemplary embodiment, the crease is closed having no freestanding width due to the friction material pressing together along the elongated crease. The insertion opening may be pressed closed by the elongated material, thereby reducing or preventing light emission from the insertion opening and requiring the elastic deformation of the elastomeric material to open the crease for insertion of the penis into the hollow channel.

Light therapy has become recognized recently as being an effective treatment to improve vascular function and is commonly used for hair loss treatment, wherein the hair follicles are stimulated. Newly emerging research reveals one of the mechanisms behind light therapy's therapeutic benefits is an increased production of ATP Adenosine triphosphate, or ATP, by mitochondria within the cell occurring after the cell is exposed to therapeutic light. ATP is the primary carrier of energy in cells. (Reference 6). It has been found that specific wavelengths of light may be particularly effective for therapy and may promote vascular function and production of ATP. Specific visible light wavelengths that have been found effective are blue and red wavelengths as shown in Table 1. A light device may also produce infrared light that has a wavelength range from about 700 nm to about 1 mm.

TABLE 1

| Visible Light Color | Wavelengths (nm) |
| --- | --- |
| Violet | 380-450 |
| Blue | 450-485 |
| Cyan | 485-500 |
| Green | 500-565 |
| Yellow | 565-590 |
| Orange | 590-625 |
| Red | 625-700 |

The light devices, may be LED lights which may be able to produce Infrared light and light in any of the visible light colors shown in Table 1 and in particular red and blue light. The LED light devices may have Chip on Board (COB) technology to enable the light wavelengths to be switched from Red to Blue and vice versa.

It may be desirable to select one wavelength or a specific combination of wavelengths depending on the therapeutic application and goals. For example, it may be desired to use red and Infrared (IR) on the penis to promote vascularization, but not use IR on the testicles since elevated temperatures have been shown to negatively impact the testes. Red and infrared light have been widely accepted for consumer product use. Red and IR light are marketed as healthy and claim to promote wellness.

Light therapy treatment of an erect penis is also ideal for the production of Nitric Oxide (NO). Blue light wavelengths have been shown to be effective in the production of Nitric Oxide plays a role in erectile health. (Reference 3) Utilizing light therapy to treat erectile dysfunction on the penis when erect will maximize localized NO production. Light therapy treatment of the penis when aroused would not be the intuitive or preferred approach of medical practitioners because of modesty in the medical profession. (Reference 13)

Blue light on the other hand has been shunned, feared, and demonized. The negative sentiment against blue light is so pervasive that products have been developed to avoid blue light such as glasses which filter out blue light (Reference 11) and software which decreases the blue light emissions from computer monitors (such as flux) and phone screens such as Apple's Night Shift. (Reference 9) Health thought leaders in the cutting edge health space have developed specialized glasses to block blue light wavelengths (truedark.com) and these glasses have become fashion statements.

Research shows that blue light inhibits melatonin production and as a consequence has been shunned and demonized by the alternative health community. (Reference 10). Given the negative sentiment in the consumer and health space with respect to blue light, a device which uses blue light is not an obvious solution to the problem of light therapy treatment of penis.

Testicles, near the base of the penis, benefit from light therapy as research demonstrates (Reference 8). Light therapy increases mitochondrial production of ATP, which makes more cellular energy available to the testicles and increases testosterone levels.

The friction-based therapeutic light penile device may be used by turning on the device to activate the light devices and then inserting the penis into the insertion opening of the hollow channel and moving the sleeve back and forth over the penis to produce friction via the friction material of the friction sleeve. The friction material may be elastomeric and may conform around the penis and elastically rebound. This will provide additional friction on the leading end, or head, of the penis when moving the sleeve back and forth. The lights of the friction-based therapeutic light penile device may be turned on prior to insertion of the penis to ensure that the friction material is warmed by the lights. During the therapy the lights devices produce an emitted light that diffuses through the friction material onto the penis within the hollow channel. The light may be dispersed by the friction material to provide full coverage of light around the penis when inserted into the sleeve.

Providing light therapy to the penis when it is stimulated is preferred because, when aroused, the organ becomes elongated and engorged with blood. The elongation and expansion of the penis provides more surface area to treat with light therapy than a non-aroused penis. The elongation also straightens out vessels, making them more accessible for light therapy delivered from an external light source. The resulting penile erection brings more blood to the area which allows for the efficient treatment of blood in addition to the organ tissues. The blood engorgement, and increased interior pressure of the corpora cavernosa, pushes vessels closer to the outer surface of the penis. The blood vessels being pushed towards the outer surface of the penis increases the amount of light that can reach the vessels because there is less distance between the vessels and the outer surface of the skin.

Light therapy treatment when the penis is erect may be preferable and more effective than light therapy on a flaccid penis. The skin of the penis is stretched during an erection, resulting in decreased tissue thickness, which allows for more therapeutic light penetration below the skin. Light therapy treatment of a non-aroused sexual organ may not be as effective as providing light therapy when the penis is erect, because the skin tissue around a flaccid penis is retracted and thicker which may reduce light penetration. Light intensity and penetration into tissues decreases dramatically with depth. Therefore, it is advantageous to treat the penis in an aroused state when the skin/mucus membrane thickness is at a minimum. The increased blood flow, increased surface area, and pushing of blood vessels closer to the organ's outer surface are all more optimal anatomical conditions for light therapy than when the penis is flaccid and not aroused. (Reference 4). Shining therapeutic light, in particular red light, has been found to in new research to increase testosterone levels. (Reference 8).

Infrared light has been shown to benefit vascular growth. In addition, infrared light lights may be selected, arranged, and powered in such a way to warm the device to approximately body temperature or slightly higher, such as about 95° F. or higher, about 97° F. or higher, about 100° F. or higher, about 105° F. or higher, about 110° F. or higher and any range between and including the temperatures provides, such as from about 95° F. to about 110° F. Furthermore, IR light may be desirable for light therapy treatment of the penis but not the scrotum and testicles. Red light and, in lesser quantities, blue light may be used for light therapy treatment of the scrotum and testicles.

The modesty of the person seeking light therapy for their sex organs makes the combining of light therapy and an erotic device a non-obvious solution. This is because people seeking sexual dysfunction treatment are not necessarily the same people who would own or use an erotic device. People having poorer health, decreased blood circulation, arterial disease and sexual dysfunction are less likely to be sexually active when compared to healthy individuals with healthy sex organs. It is not obvious that people with sub-optimal sexual function would use erotic devices.

A vacuum device (aka penis pump) is utilized for stimulation of the penis to engorge the penis for pleasure and for increasing the size of the penis. While therapeutic lights may be incorporated into one of these non-contact penis enlargement implements, the friction-based therapeutic light penile device is preferred. The direct stimulation via friction of the penis, as opposed to indirect stimulation created by a vacuum device is preferred as vacuums can change to the shape, size, and even coloration of the penis. Also, penis pumps can also damage blood vessels. A user may not want to subject risk these possible effects in order to receive penile light therapy and treat erectile dysfunction.

To maximize the utilization of light being emitted, a white or reflective material could be placed along the inside wall of the outer shell, or behind a light device or light producing portion of the light device. Emitted light may pass through the friction material, through the hollow channel through the friction material on the opposing side and then reflect off the reflective material on the outer shell. The reflective material may be a coating, such as paint or pigment, or may be thin film or layer of material, such as a foil or mirror coated film, or white film for example. Reflective material may also be configured on the flange and may also reflect back or reflect light from other light devices.

To further stimulate blood flow to the penis, a friction-based therapeutic light penile device may have a vibratory device, such as an offset weight oscillating or rotating motor device that produces a vibration that can be tuned to a desired frequency by changing the oscillation frequency or speed of the motor, revolutions per minute (RPM). The vibration device may be coupled with the outer shell as this rigid component may transfer the vibration across the friction-based therapeutic light penile device.

Elastomeric material, as used herein, is a material that can be deformed by a force and will substantially return, within about 20% of a deflected shape, to an original shape upon removal of the deforming force within about 1 hour.

An exemplary friction material may be silicone or polydimethylsiloxane which may be an elastic material as defined herein. The polymers listed in Table 2 have an index of refraction, or refractive index that is substantially the same as water and may be suitable candidates for diffusing the light from the light devices.

TABLE 2

| Polymer | Refractive Index |
| --- | --- |
| Dimethyl silicone rubber | 1.4 |
| Methyl phenyl silicone rubber | 1.40-1.60 |
| Poly(hexafluoropropylene oxide) | 1.301 |
| Poly(tetrafluoroethylene-co-hexafluoropropylene) | 1.338 |
| Poly(pentadecafluorooctyl acrylate) | 1.339 |
| Poly(tetrafluoro-3-(heptafluoropropoxy)propyl acrylate) | 1.346 |
| Poly(tetrafluoro-3-(pentafluoroethoxy)propyl acrylate) | 1.348 |
| Poly(tetrafluoroethylene) | 1.35 |
| Poly(undecafluorohexyl acrylate) | 1.356 |
| Poly(nonafluoropentyl acrylate) | 1.36 |
| Poly(tetrafluoro-3-(trifluoromethoxy)propyl acrylate) | 1.36 |
| Poly(pentafluorovinyl propionate) | 1.364 |
| Poly(heptafluorobutyl acrylate) | 1.367 |
| Poly(trifluorovinyl acetate) | 1.375 |
| Poly(octafluoropentyl acrylate) | 1.38 |
| Poly(methyl 3,3,3-trifluoropropyl siloxane) | 1.383 |
| Poly(pentafluoropropyl acrylate) | 1.385 |
| Poly(2-heptafluorobutoxy)ethyl acrylate) | 1.39 |
| Poly(chlorotrifluoroethylene) | 1.39 |
| Poly(2,2,3,4,4-hexafluorobutyl acrylate) | 1.392 |
| Poly(methyl hydro siloxane) | 1.397 |
| Poly(methacrylic acid), sodium salt | 1.401 |
| Poly(dimethyl siloxane) | 1.4035 |
| Poly(trifluoroethyl acrylate) | 1.407 |
| Poly(2-(1,1,2,2-tetrafluoroethoxy)ethyl acrylate | 1.412 |
| Poly(trifluoroisopropyl methacrylate) | 1.4177 |
| Poly(2,2,2-trifluoro-1-methylethyl methacrylate) | 1.4185 |
| Poly(2-trifluoroethoxyethyl acrylate) | 1.419 |
| Poly(vinylidene fluoride) | 1.42 |
| Poly(trifluoroethyl methacrylate) | 1.437 |
| Poly(methyl octadecyl siloxane) | 1.443 |
| Poly(methyl hexyl siloxane) | 1.443 |
| Poly(methyl octyl siloxane) | 1.445 |
| Poly(isobutyl methacrylate) | 1.447 |
| Poly(vinyl isobutyl ether) | 1.4507 |
| Poly(methyl hexadecyl siloxane) | 1.451 |
| Poly(ethylene oxide) | 1.4539 |
| Poly(vinyl ethyl ether) | 1.454 |
| Poly(methyl tetradecyl siloxane) | 1.455 |
| Poly(ethylene glycol mono-methyl ether) | 1.4555 |
| Poly(vinyl n-butyl ether) | 1.4563 |
| Poly(propylene oxide) | 1.457 |
| Poly(3-butoxypropylene oxide) | 1.458 |
| Poly(3-hexoxypropylene oxide) | 1.459 |
| Poly(ethylene glycol) | 1.459 |
| Poly(vinyl n-pentyl ether) | 1.459 |
| Poly(vinyl n-hexyl ether) | 1.4591 |
| Poly(4-fluoro-2-trifluoromethylstyrene) | 1.46 |
| Poly(vinyl octyl ether) | 1.4613 |
| Poly(vinyl n-octyl acrylate) | 1.4613 |
| Poly(vinyl 2-ethylhexyl ether) | 1.4626 |
| Poly(vinyl n-decyl ether) | 1.4628 |
| Poly(2-methoxyethyl acrylate) | 1.463 |
| Poly(acryloxypropyl methyl siloxane) | 1.463 |

TABLE 2-continued

| Polymer | Refractive Index |
|---|---|
| Poly(4-methyl-1-pentene) | 1.463 |
| Poly(3-methoxypropylene oxide) | 1.463 |
| Poly(t-butyl methacrylate) | 1.4638 |
| Poly(vinyl n-dodecyl ether) | 1.464 |
| Poly(3-ethoxypropyl acrylate) | 1.465 |
| Poly(vinyl propionate) | 1.4664 |
| Poly(vinyl acetate) | 1.4665 |
| Poly(vinyl propionate) | 1.4665 |
| Poly(vinyl methyl ether) | 1.467 |
| Poly(ethyl acrylate) | 1.4685 |
| Poly(vinyl methyl ether) (isotactic) | 1.47 |
| Poly(3-methoxypropyl acrylate) | 1.471 |
| Poly(1-octadecene) | 1.471 |
| Poly(2-ethoxyethyl acrylate) | 1.471 |
| Poly(isopropyl acrylate) | 1.4728 |
| Poly(1-decene) | 1.473 |
| Poly(propylene) (atactic) | 1.4735 |
| Poly(lauryl methacrylate) | 1.474 |
| Poly(vinyl sec-butyl ether) (isotactic) | 1.474 |
| Poly(n-butyl acrylate) | 1.474 |
| Poly(dodecyl methacrylate) | 1.474 |
| Poly(ethylene succinate) | 1.4744 |
| Poly(tetradecyl methacrylate) | 1.4746 |
| Poly(hexadecyl methacrylate) | 1.475 |
| Cellulose acetate butyrate | 1.475 |
| Cellulose acetate | 1.475 |
| Poly(vinyl formate) | 1.4757 |
| Ethylene/vinyl acetate copolymer-40% vinyl acetate | 1.476 |
| Poly(2-fluoroethyl methacrylate) | 1.4768 |
| Poly(octyl methyl silane) | 1.478 |
| Ethyl cellulose | 1.479 |
| Poly(methyl acrylate) | 1.4793 |
| Poly(dicyanopropyl siloxane) | 1.48 |
| Poly(oxymethylene) | 1.48 |
| Poly(sec-butyl methacrylate) | 1.48 |
| Poly(dimethylsiloxane-co-alpha-methyl styrene) | 1.48 |
| Poly(n-hexyl methacrylate) | 1.4813 |
| Ethylene/vinyl acetate copolymer-33% vinyl acetate | 1.482 |
| Poly(n-butyl methacrylate) | 1.483 |
| Poly(ethylidene dimethacrylate) | 1.4831 |
| Poly(2-ethoxyethyl methacrylate) | 1.4833 |
| Poly(n-propyl methacrylate) | 1.484 |
| Poly(ethylene maleate) | 1.484 |
| Ethylene/vinyl acetate copolymer-28% vinyl acetate | 1.4845 |
| Poly(ethyl methacrylate) | 1.485 |
| Poly(vinyl butyral) | 1.485 |
| Poly(vinyl butyral)-11% hydroxyl | 1.485 |
| Poly(3,3,5-trimethylcyclohexyl methacrylate) | 1.485 |
| Poly(2-nitro-2-methylpropyl methacrylate) | 1.4868 |
| Poly(dimethylsiloxane-co-diphenylsiloxane) | 1.488 |
| Poly(1,1-diethylpropyl methacrylate) | 1.4889 |
| Poly(triethylcarbinyl methacrylate) | 1.4889 |
| Poly(methyl methacrylate) | 1.4893 |
| Poly(2-decyl-1,4-butadiene) | 1.4899 |
| Polypropylene, isotactic | 1.49 |
| Poly(vinyl butyral)-19% hydroxyl | 1.49 |
| Poly(mercaptopropyl methyl siloxane) | 1.49 |
| Poly(ethyl glycolate methacrylate) | 1.4903 |
| Poly(3-methylcyclohexyl methacrylate) | 1.4947 |
| Poly(cyclohexyl alpha-ethoxyacrylate) | 1.4969 |
| Methyl cellulose | 1.497 |
| Poly(4-methylcyclohexyl methacrylate) | 1.4975 |
| Poly(decamethylene glycol dimethacrylate) | 1.499 |
| Poly(vinyl alcohol) | 1.5 |
| Poly(vinyl formal) | 1.5 |
| Poly(2-bromo-4-trifluoromethyl styrene) | 1.5 |
| Poly(1,2-butadiene) | 1.5 |
| Poly(sec-butyl alpha-chloroacrylate) | 1.5 |
| Poly(2-heptyl-1,4-butadiene) | 1.5 |
| Poly(vinyl methyl ketone) | 1.5 |
| Poly(ethyl alpha-chloroacrylate) | 1.502 |
| Poly(vinyl formal) | 1.502 |
| Poly(2-isopropyl-1,4-butadiene) | 1.502 |
| Poly(2-methylcyclohexyl methacrylate) | 1.5028 |
| Poly(bornyl methacrylate) | 1.5059 |
| Poly(2-t-butyl-1,4-butadiene) | 1.506 |
| Poly(ethylene glycol dimethacrylate) | 1.5063 |
| Poly(cyclohexyl methacrylate) | 1.5065 |
| Poly(cyclohexanediol-1,4-dimethacrylate) | 1.5067 |
| Butyl rubber (unvulcanized) | 1.508 |
| Gutta percha b | 1.509 |
| Poly(tetrahydrofurfuryl methacrylate) | 1.5096 |
| Poly(isobutylene) | 1.51 |
| Polyethylene, low density | 1.51 |
| Ethylene/methacrylic acid ionomer, sodium ion | 1.51 |
| Polyethylene | 1.51 |
| Cellulose nitrate | 1.51 |
| Polyethylene Ionomer | 1.51 |
| Polyacetal | 1.51 |
| Poly(1-methylcyclohexyl methacrylate) | 1.5111 |
| Poly(2-hydroxyethyl methacrylate) | 1.5119 |
| Poly(1-butene) (isotactic) | 1.5125 |
| Poly(vinyl methacrylate) | 1.5129 |
| Poly(vinyl chloroacetate) | 1.513 |
| Poly(N-butyl methacrylamide) | 1.5135 |
| Gutta percha a | 1.514 |
| Poly(2-chloroethyl methacrylate) | 1.517 |
| Poly(methyl alpha-chloroacrylate) | 1.517 |
| Poly(2-diethylaminoethyl methacrylate) | 1.5174 |
| Poly(2-chlorocyclohexyl methacrylate) | 1.5179 |
| Poly(1,4-butadiene) (35% cis; 56% trans; 7% 1,2-content) | 1.518 |
| Poly(acrylonitrile) | 1.5187 |
| Poly(isoprene), cis | 1.5191 |
| Poly(allyl methacrylate) | 1.5196 |
| Poly(methacrylonitrile) | 1.52 |
| Poly(methyl isopropenyl ketone) | 1.52 |
| Poly(butadiene-co-acrylonitrile) | 1.52 |
| Poly(2-ethyl-2-oxazoline) | 1.52 |
| Poly(1,4-butadiene) (high cis-type) | 1.52 |
| Poly(N-2-methoxyethyl)methacrylamide | 1.5246 |
| Poly(2,3-dimethylbutadiene) [methyl rubber] | 1.525 |
| Poly(2-chloro-1-(chloromethyl)ethyl methacrylate) | 1.527 |
| Poly(1,3-dichloropropyl methacrylate) | 1.527 |
| Poly(acrylic acid) | 1.527 |
| Poly(N-vinyl pyrrolidone) | 1.53 |
| Nylon 6 [Poly(caprolactam)] | 1.53 |
| Poly(butadiene-co-styrene) (30% styrene) block copolymer | 1.53 |
| Poly(cyclohexyl alpha-chloroacrylate) | 1.532 |
| Poly(methyl phenyl siloxane) | 1.533 |
| Poly(2-chloroethyl alpha-chloroacrylate) | 1.533 |
| Poly(butadiene-co-styrene) (75/25) | 1.535 |
| Poly(2-aminoethyl methacrylate) | 1.537 |
| Poly(furfuryl methacrylate) | 1.5381 |
| Poly(vinyl chloride) | 1.539 |
| Poly(butylmercaptyl methacrylate) | 1.539 |
| Poly(1-phenyl-n-amyl methacrylate) | 1.5396 |
| Poly(N-methyl methacrylamide) | 1.5398 |
| Polyethylene, high density | 1.54 |
| Cellulose | 1.54 |
| Poly(cyclohexyl alpha-bromoacrylate) | 1.542 |
| Poly(sec-butyl alpha-bromoacrylate) | 1.542 |
| Poly(2-bromoethyl methacrylate) | 1.5426 |
| Poly(dihydroabietic acid) | 1.544 |
| Poly(abietic acid) | 1.546 |
| Poly(ethylmercaptyl methacrylate) | 1.547 |
| Poly(N-allyl methacrylamide) | 1.5476 |
| Poly(1-phenylethyl methacrylate) | 1.5487 |
| Poly(2-vinyltetrahydrofuran) | 1.55 |
| Poly(vinylfuran) | 1.55 |
| Poly(methyl m-chlorophenylethyl siloxane) | 1.55 |
| Poly(p-methoxybenzyl methacrylate) | 1.552 |
| Poly(isopropyl methacrylate) | 1.552 |
| Poly(p-isopropyl styrene) | 1.554 |
| Poly(isoprene), chlorinated | 1.554 |
| Poly(p,p'-xylylenyl dimethacrylate) | 1.5559 |
| Poly(cyclohexyl methyl silane) | 1.557 |
| Poly(1-phenylallyl methacrylate) | 1.5573 |

TABLE 2-continued

| Polymer | Refractive Index |
|---|---|
| Poly(p-cyclohexylphenyl methacrylate) | 1.5575 |
| Poly(chloroprene) | 1.558 |
| Poly(2-phenylethyl methacrylate) | 1.5592 |
| Hydroxypropyl cellulose | 1.56 |
| Poly(methyl m-chlorophenyl siloxane) | 1.56 |
| Poly[4,4-heptane bis(4-phenyl)carbonate)] | 1.5602 |
| Poly[1-(o-chlorophenyl)ethyl methacrylate)] | 1.5624 |
| Styrene/maleic anhydride copolymer | 1.564 |
| Poly(1-phenylcyclohexyl methacrylate) | 1.5645 |
| Nylon 6,10 [Poly(hexamethylene sebacamide)] | 1.565 |
| Nylon 6,6 [Poly(hexamethylene adipamide)] | 1.565 |
| Nylon 6(3)T [Poly(trimethyl hexamethylene terephthalamide)] | 1.566 |
| Poly(2,2,2'-trimethylhexamethylene terephthalamide) | 1.566 |
| Poly(methyl alpha-bromoacrylate) | 1.5672 |
| Poly(benzyl methacrylate) | 1.568 |
| Poly[2-(phenylsulfonyl)ethyl methacrylate] | 1.5682 |
| Poly(m-cresyl methacrylate) | 1.5683 |
| Styrene/acrylonitrile copolymer | 1.57 |
| Poly(o-methoxyphenol methacrylate) | 1.5705 |
| Poly(phenyl methacrylate) | 1.5706 |
| Poly(o-cresyl methacrylate) | 1.5707 |
| Poly(diallyl phthalate) | 1.572 |
| Poly(2,3-dibromopropyl methacrylate) | 1.5739 |
| Poly(2,6-dimethyl-p-phenylene oxide) | 1.575 |
| Poly(ethylene terephthalate) | 1.575 |
| Poly(vinyl benozoate) | 1.5775 |
| Poly[2,2-propane bis[4-(2-methylphenyl)]carbonate] | 1.5783 |
| Poly[1,1-butane bis(4-phenyl)carbonate] | 1.5792 |
| Poly(1,2-diphenylethyl methacrylate) | 1.5816 |
| Poly(o-chlorobenzyl methacrylate) | 1.5823 |

Reference 1:

Laser photobiomodulation of wound healing: a review of experimental studies in mouse and rat animal models, Peplow P V, Chung T Y, Baxter G D. Laser photobiomodulation of wound healing: a review of experimental studies in mouse and rat animal models. Photomed Laser Surg. 2010 June; 28(3):291-325. doi: 10.1089/pho.2008.2446. PMID: 19995230., https://pubmed.ncbi.nlm.nih.gov/19995230/

Reference 2:

Physiology of Penile Erection and Pathophysiology of Erectile Dysfunction Urol Clin North Am. Author manuscript; available in PMC 2006 Jan. 25. Published in final edited form as: Urol Olin North Am. 2005 November; 32(4): 379-v. Doi: 10.1016/j.ucl.2005.08.007 PMCID: PMC1351051, NIHMSID: NIHMS6980, PMID: 16291031, https://www.ncbi.nlm.nih.gov/pmc/articles/PMC1351051/

Reference 3:

Low level light therapy by LED of different wavelength induces angiogenesis and improves ischemic wound healing, Dungel P, Hartinger J, Chaudary S, Slezak P, Hofmann A, Hausner T, Strassl M, Wintner E, Redl H, Mittermayr R. Low level light therapy by LED of different wavelength induces angiogenesis and improves ischemic wound healing. Lasers Surg Med. 2014 December; 46(10):773-80. doi: 10.1002/lsm.22299. Epub 2014 Oct. 31. PMID: 25363448. https://pubmed.ncbi.nlm.nih.gov/25363448/

Background and objective: Low-level light therapy (LLLT) has been revealed as a potential means to improve wound healing. So far, most studies are being performed with irradiation in the red to near-infrared spectra. Recently, we showed that blue light (470 nm) can significantly influence biological systems such as nitric oxide (NO) metabolism and is able to release NO from nitrosyl-hemoglobin or mitochondrial protein complexes. Therefore, the aim of this study was to evaluate and compare the therapeutic value of blue or red light emitting diodes (LEDs) on wound healing in an ischemia disturbed rodent flap model.

Conclusions: LED treatment of ischemia challenged tissue improved early wound healing by enhancing angiogenesis irrespective of the wavelength thus delineating this noninvasive means as a potential, cost effective tool in complicated wounds.

Reference 4:

Biomechanics of male erectile function J. R. Soc. Interface (2007) 4, 1031-1047 doi:10.1098/rsif.2007.0221 Published online 3 May 2007, 22 Dec. 2007, Volume 4 Issue 17, https://royalsocietypublishing.org/doi/10.1098/rsif.2007.0221

Reference 5:

Sexual Function Is an Indicator of Central Arterial Stiffness and Arterial Stiffness Gradient in Japanese Adult Men, Originally published 5 May 2018, https://doi.org/10.1161/JAHA.117.007964 Journal of the American Heart Association.;7:e007964, About the correlation between atherosclerosis and erectile dysfunction, https://www.ahajournals.org/doi/10.1161/JAHA.117.007964

Reference 6:

Low-Intensity Light Therapy: Exploring the Role of Redox Mechanisms, Tafur, J., & Mills, P. J. (2008). Low-intensity light therapy: exploring the role of redox mechanisms. *Photomedicine and laser surgery*, 26(4), 323-328. https://doi.org/10.1089/pho.2007.2184, https://www.ncbi.nlm.nih.gov/pmc/articles/PMC2996814/

Reference 7:

Low-Level Laser (Light) Therapy (LLLT) in skin: stimulating, healing, restoring Avci, Pinar & Gupta, Asheesh & Sadasivam, Magesh & Vecchio, Daniela & Pam, Zeev & Pam, Nadav & Hamblin, Michael. (2013). Low-Level Laser (Light) Therapy (LLLT) in skin: stimulating, healing, restoring. Seminars in cutaneous medicine and surgery. 32. 41-52. https://www.researchgate.net/publication/256835631_Low Level_Laser_Light_Therapy_LLLT_in_skin_stimulating_healing_restoring Reference 8:

Effectiveness of low level laser therapy for treating male infertility Vladimirovich Moskvin S, Ivanovich Apolikhin O. Effectiveness of low level laser therapy for treating male infertility. Biomedicine (Taipei). 2018 June;8(2):7. doi: 10.1051/bmdcn/2018080207. Epub 2018 May 28. PMID: 29806585; PMCID: PMC5992952. https://www.ncbi.nlm.nih.gov/pmc/articles/PMC5992952/

Reference 9:

https://en.m.wikipedia.org/wiki/Night_Shift_(software), "Night Shift is a built in software feature of iOS and macOS. It was introduced into iOS in iOS 9.3 and into macOS in macOS Sierra 10.12.4.[1] The feature changes the color temperature of the display towards the yellowish part of the color spectrum[2] that reduces some of the blue light from the screen.[3] Apple claims that the feature may help users have a better night's sleep by filtering blue wavelengths from the display.[4] The effectiveness of this feature is disputed.[5] The feature is similar to the functionality flux provides.[6][7]"

Reference 10: Strategies to decrease social jetlag: Reducing evening blue light advances sleep and melatonin, Giulia Zerbini et al. Eur J Neurosci. 2020 June Zerbini G, Kantermann T, Merrow M. Strategies to decrease social jetlag: Reducing evening blue light advances sleep and melatonin. Eur J Neurosci. 2020 June;51(12):2355-2366. doi: 10.1111/ejn.14293. Epub 2018 Dec. 13. PMID: 30506899. https://pubmed.ncbi.nlm.nih.gov/30506899/

Reference 11:

Blue-Light Filtering Spectacle Lenses: Optical and Clinical Performances, Tsz Wing Leung et al. PLoS One. 2017., Leung T W, Li R W, Kee C S. Blue-Light Filtering Spectacle Lenses: Optical and Clinical Performances. PLoS One. 2017 Jan. 3; 12(1):e0169114. doi: 10.1371/journal.pone.0169114. PMID: 28045969; PMCID: PMC5207664

Reference 12:

Cartledge J, Minhas S, Eardley I. The role of nitric oxide in penile erection. Expert Opin Pharmacother. 2001 January; 2(1):95-107. doi: 10.1517/14656566.2.1.95. PMID: 11336572.

Reference 13:

Low-level laser treatment with near-infrared light increases venous nitric oxide levels acutely: a single-blind, randomized clinical trial of efficacy, "The peak increase in NO occurred 5 mins into the treatment", Mitchell U H, Mack G L. Low-level laser treatment with near-infrared light increases venous nitric oxide levels acutely: a single-blind, randomized clinical trial of efficacy. Am J Phys Med Rehabil. 2013 February;92(2):151-6. doi: 10.1097/PHM.0b013e318269d70a. PMID: 23334615.

Reference 14:

Clitoral blood flow increases following vaginal pressure stimulation, https://pubmed.ncbi.nlm.nih.gov/7733803/Lavoisier P, Aloui R, Schmidt M H, Watrelot A. Clitoral blood flow increases following vaginal pressure stimulation. Arch Sex Behav. 1995 February;24(1):37-45. doi: 10.1007/BF01541987. PMID: 7733803.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Referring now to FIGS. 1 to 4, a friction-based therapeutic light penile device 10 has a sleeve 30 for insertion of the penis 16 therein and one or more therapeutic light devices 80 configured to emit an emitted light 82 onto the penis while in the sleeve. As described herein, the emitted light is preferably a red wavelength light, or light having a wavelength from about 625 nm to 700 nm. The sleeve 30 has an outer shell 31 configured around a portion of the outside surface 32 and a friction sleeve 40 configured therein. The friction sleeve may be an elastomeric material 42, as defined herein, such as silicone or polyurethane, and may deform around the inserted penis to provide friction. In addition, the friction sleeve is a translucent material that allows the emitted light to pass therethrough to the outer surface of the penis and/or to the scrotum.

The friction sleeve, forms the inside surface 44 of the hollow channel 33, configured for insertion and arousal of an erect penis. The friction material 41 of the friction sleeve 40, such as an elastomeric material 42 may extend radially out from the outer shell and form an insertion flange 45. The insertion flange may be shaped to resemble a vagina for further stimulation and arousal. The insertion flange may form an elongated crease 46 that is closed by the pressing of the elastomeric material from opposing sides of the crease. This sealed crease may reduce and/or prevent light from being emitted from the insertion opening 35. The erect penis may be inserted through this elongated crease to deform the elastomeric material and allow penetration into the hollow channel.

Figure 1:
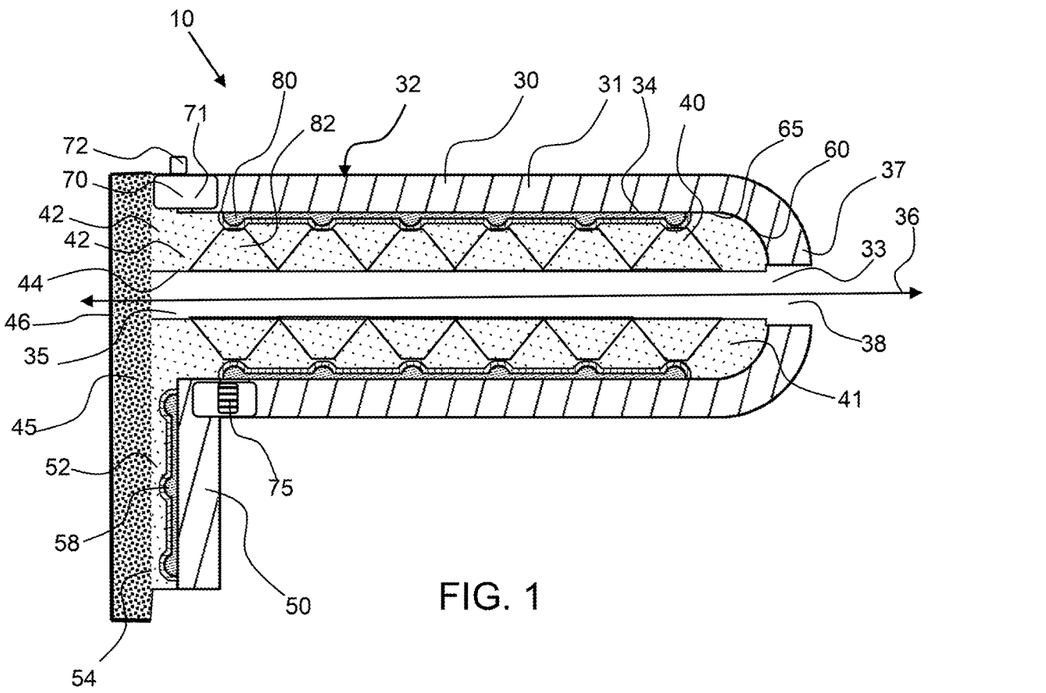
FIG. 1 shows a cross sectional view of a friction-based therapeutic light penile device having a sleeve for insertion of the penis and one or more therapeutic light devices configured to emit an emitted light onto the penis while in the sleeve and wherein the light is preferably a red wavelength light, or light having a wavelength from about 625 nm to 700 nm.
Figure 2:
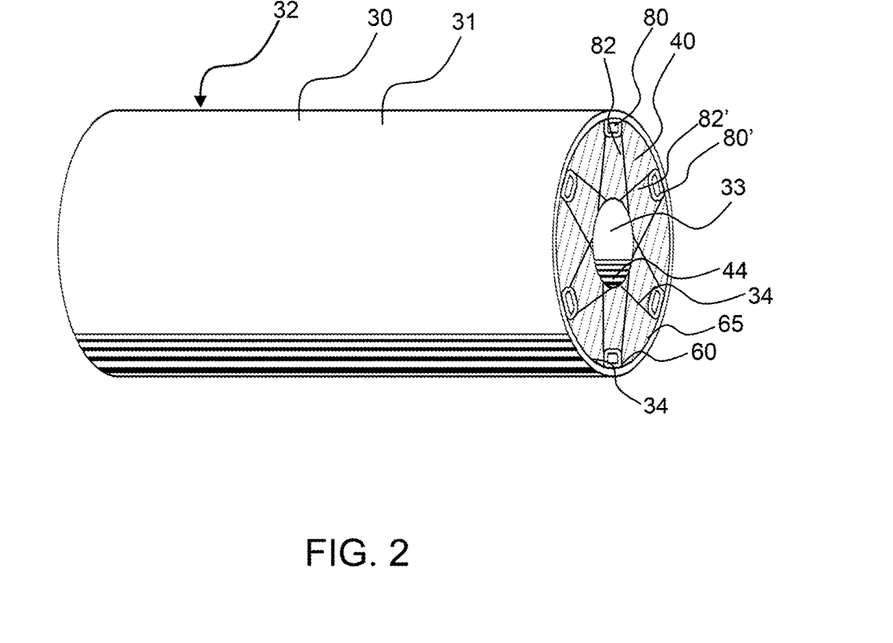
FIG. 2 shows perspective view of a portion of the sleeve of showing that lights are configured around the circumference of the sleeve.

As shown, the light devices 80 are configured proximal to the outer shell 31 and may be coupled to the outer shell, thereby providing an offset distance 87 from the light to the inside surface 34 of the of the sleeve 30. This offset distance may enable the light to diffuse outward to provide substantially full coverage over a portion of the length of the sleeve along the inside surface of the sleeve. Substantial full coverage means that light is emitted from at least 80% of an extension of the inside surface and preferably at least 90%. The light devices may be configured to produce an emitted light that overlaps with another adjacent light device along the length of the sleeve and/or around the circumference of the sleeve. As shown in FIG. 1, the emitted light 82 is overlapping along the inside surface 34 from lights configured along the length of the sleeve, or along a length axis 36. Also, as shown in FIG. 2, the light devices 80, 80' configured around the circumference of the sleeve, a circumferential offset angle, are configured to produce overlapping emitted light 82, 82', respectively, along the circumference of the inside surface 34. This combination of overlapping emitted light along the length axis and along the circumferences provides substantially full coverage of a portion of the sleeve, not including the insertion opening 35 and the extended end 37. With reference to FIGS. 1 and 2, the plurality of lights are configured in rows, wherein a first row of light devices extend in a first row along the length axis 36 of the sleeve 30 and a second row of lights is configured in a second row a circumferential angle offset from said first row.

As shown in FIG. 1, a waterproof seal 60 may be configured between the friction sleeve 40 and the light devices 80 to prevent damage to the light devices. The sleeve may have an insertion opening 35 for insertion of the penis and an extended end opening 38 on the extended end 37 to allow easy cleaning by running water through the hollow channel 33.

As shown in FIGS. 1 to 4, the friction-based therapeutic light penile device may include a reflective material 65 configured along the inside surface 34 of the outer shell 32. The reflective material may reflect emitted light 82 from the light devices 80 back toward the hollow channel 33.

As shown in FIG. 1, the friction-based therapeutic light penile device 10 has a testicular flange 50 that extends down from the sleeve 30 and comprises flange lights 58 to emit an emitted light onto the scrotum. The outer shell 31 may extend down to from a portion of the testicular flange. The testicular flange may also have flange friction material 54, such as an elastomeric material 52 for comfort during therapy.

As shown in FIG. 1, a vibratory device 75 may be configured to produce vibrations of the sleeve and testicular flange 50. This vibratory device and the light devices 80 may be powered by a power source 71, such as a battery 70. An on/off switch 72 may be used to initiate the light devices and/or the vibratory device.

As shown in FIG. 2, the light devices 80, 80' are configured around the circumference of the sleeve 30 and are producing circumferential overlapping emitted light 82, 82' on the inside surface 34 of the sleeve. The outer shell 31 may be a rigid material that is opaque to prevent light from being emitted therethrough.

Figure 3:
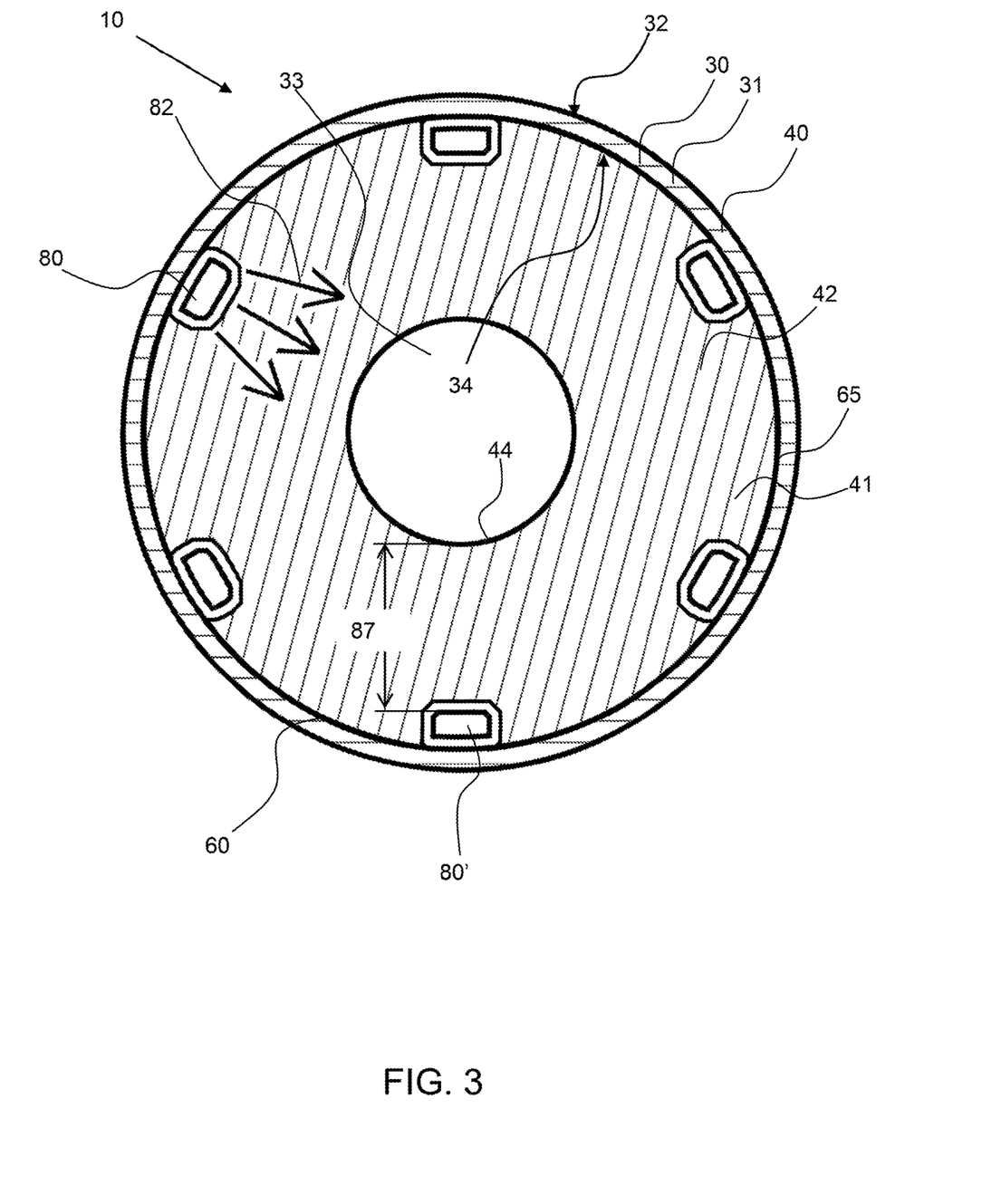
FIG. 3 shows a cross sectional view of a friction-based therapeutic light penile device having a sleeve for insertion of the penis and one or more therapeutic lights configured to emit an emitted light onto the penis while in the sleeve.

As shown in FIG. 3, the friction sleeve 40 extends from the outer shell 31 to the inside surface 34 of the sleeve. This produces an offset distance 87 from the light device 80' and the inside surface. As described herein, this offset distance may enable the light to diffuse and spread to produce a greater area of coverage on the penis when inserted into the sleeve. The light devices 80 are coupled to the inside surface of the outer shell 31. The outside surface 32 is cylindrical and formed by the outer shell which may be more rigid and may be opaque to prevent light transmission therethrough.

Figure 4:
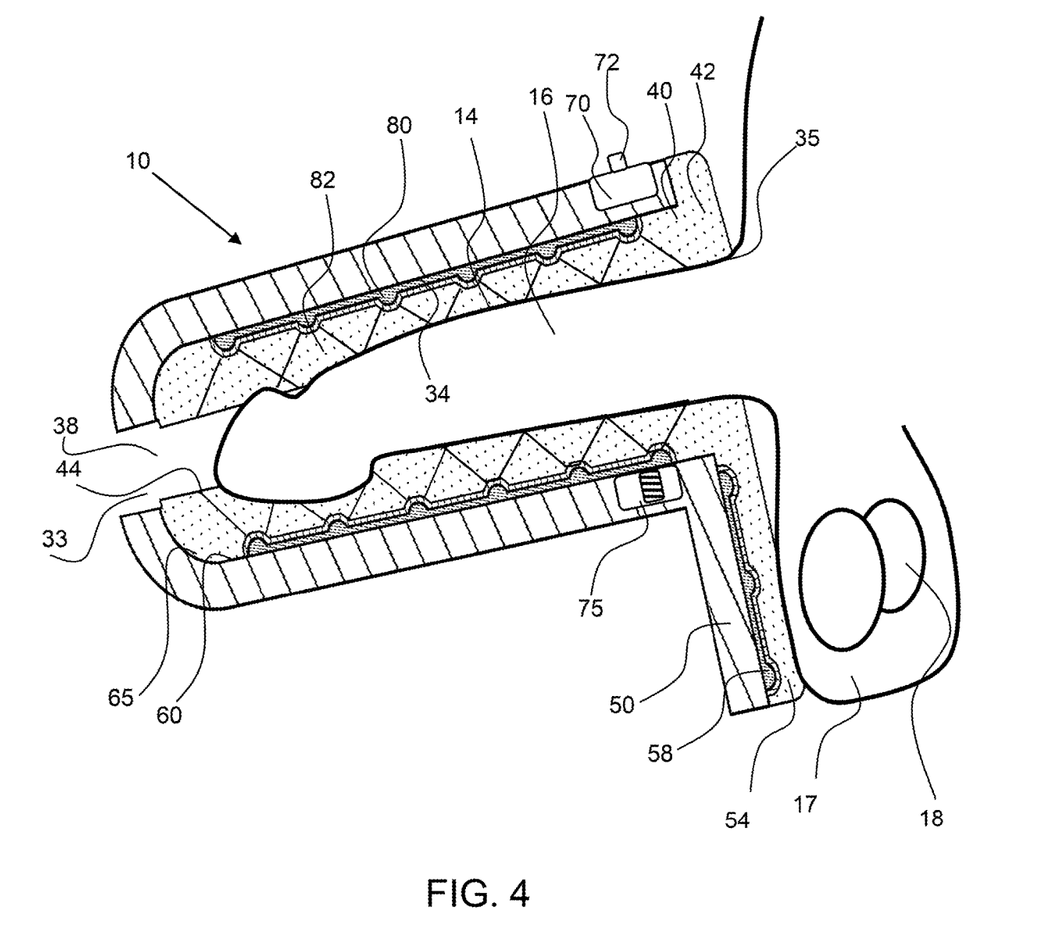
FIG. 4 shows a cross sectional view of a friction-based therapeutic light penile device having a sleeve and an erect penis configured within the sleeve wherein the therapeutic emitted light is incident on the penis and on the scrotum.

As shown in FIG. 4, a penis 16 is inserted into the sleeve 30 and is deforming the friction sleeve 40, which is an elastomeric material 42 such as silicone or urethane having high light transmission. The light devices 80 are emitting an emitted light 82 onto the outside surface of the penis, or onto the skin 14, and the flange lights 58 are emitting light onto the scrotum 17 from the testicular flange 50 portion of the device. As described herein, incident light on the engorged penis with the blood vessels expanded may be more effective and promote increased blood flow for the treatment of erectile dysfunction.

Figure 5:
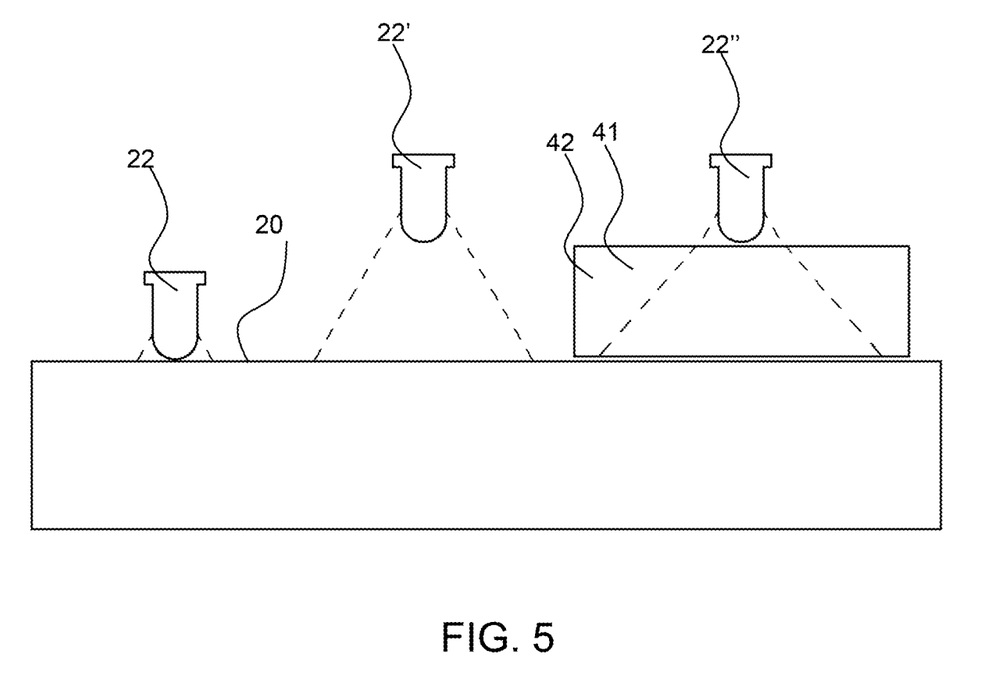
FIG. 5 shows a diagram of light dispersion as a function of distance from a target surface and through a diffusing material.

As shown in FIG. 5, light sources 22, 22' and 22" produce an emitted light that has a dispersed light size on a target surface 20. The light source 22' is configured an offset distance from the target surface and therefore has a larger dispersed light area on the target surface. The light source 22" is emitting light through a diffusing material, such as a translucent friction material 41 and in particular a translucent elastomeric material 42 and is being further disperse to produce an even larger area on the target surface. This principal is incorporated into the friction-based therapeutic light penile device as described herein.

Figure 6:
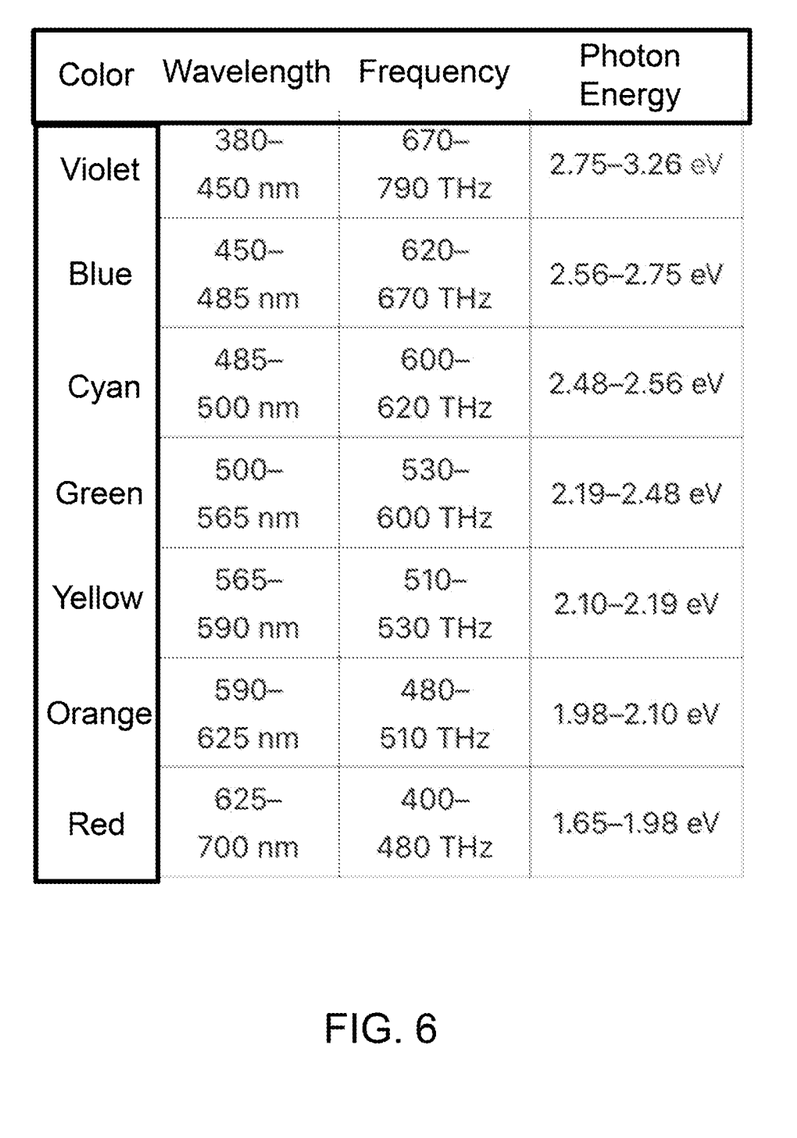
FIG. 6 shows a table of wavelength, frequency and photon energy for various colors of light in the light spectrum.

FIG. 6 shows a table of wavelength, frequency and photon energy for various colors of light in the light spectrum.

Figure 7:
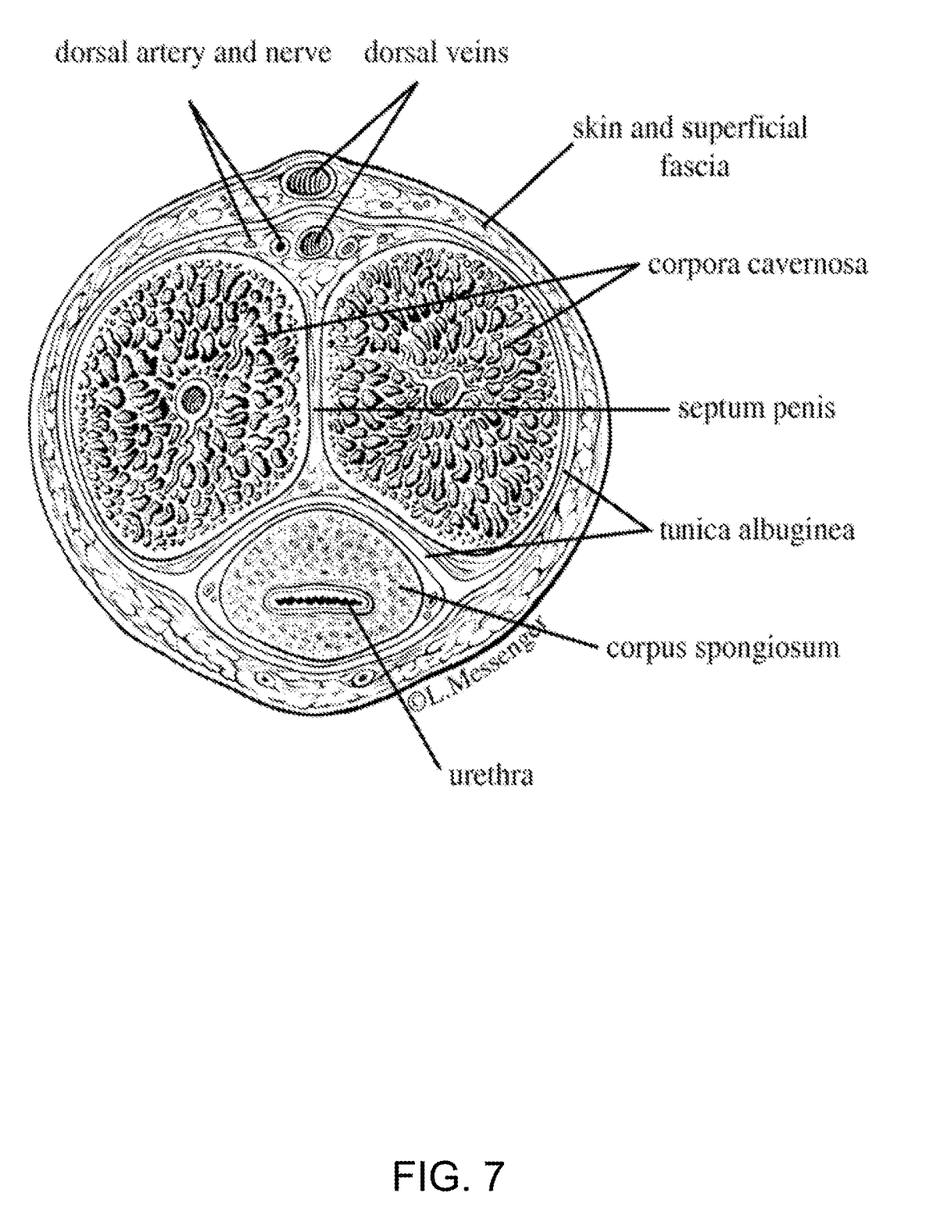
FIG. 7 shows a cross sectional view of the penis.

FIG. 7 shows a cross sectional view of the penis.

Figure 8:
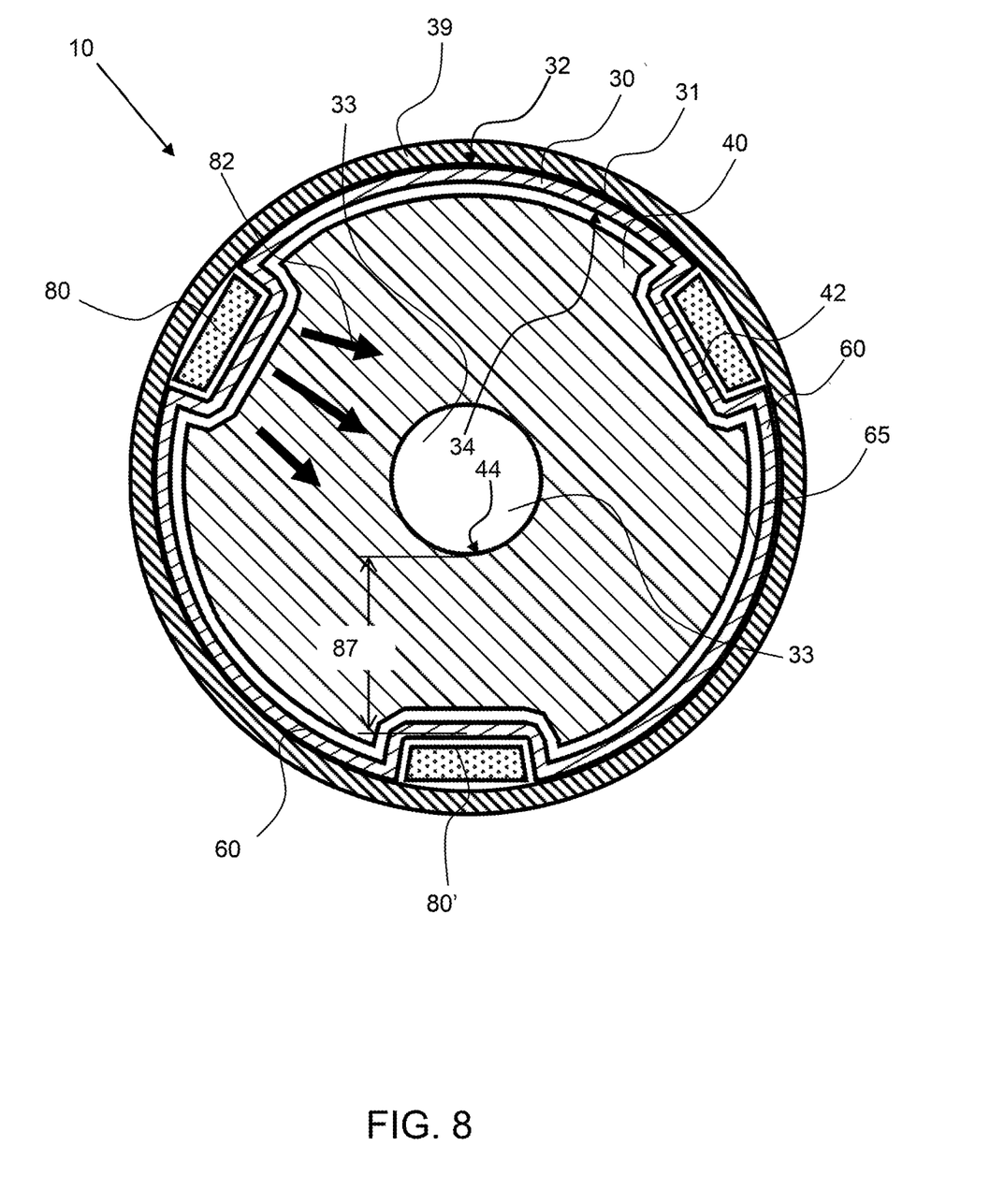
FIG. 8 shows a cross sectional view of a friction-based therapeutic light penile device having a sleeve for insertion of the penis and one or more therapeutic lights configured to emit an emitted light onto the penis while in the sleeve.

As shown in FIG. 8, a friction-based therapeutic light penile device 10 has a sleeve 30 for insertion of the penis 16 therein and one or more therapeutic light devices 80 configured to emit an emitted light 82 onto the penis while in the sleeve. As described herein, the emitted light is preferably a red wavelength light, or light having a wavelength from about 625 nm to 700 nm. The sleeve 30 has an outer shell 31 configured around a portion of the outside surface 32 and a friction sleeve 40 configured therein. The therapeutic light devices 80 is configured radially outside of the sleeve 30 in recesses in the sleeve 30. The sleeve may be rigid, wherein it maintains a shape and is free standing and may have defined recesses or channels for receiving the therapeutic light devices 80. The friction sleeve may be an elastomeric material 42, as defined herein, such as silicone or polyurethane, and may deform around the inserted penis to provide friction. In addition, the friction sleeve is a translucent material that allows the emitted light to pass therethrough to the outer surface of the penis and/or to the scrotum.

The friction sleeve, forms the inside surface 44 of the hollow channel 33, configured for insertion and arousal of an erect penis. The friction material 41 of the friction sleeve 40, such as an elastomeric material 42 may extend radially out from the outer shell and form an insertion flange 45. The insertion flange may be shaped to resemble a vagina for further stimulation and arousal. The insertion flange may form an elongated crease 46 that is closed by the pressing of the elastomeric material from opposing sides of the crease. This sealed crease may reduce and/or prevent light from being emitted from the insertion opening 35. The erect penis may be inserted through this elongated crease to deform the elastomeric material and allow penetration into the hollow channel.

As shown in FIG. 8, the light devices 80 are configured proximal to the outer shell 31 and may be coupled to the outer shell, thereby providing an offset distance 87 from the light to the inside surface 34 of the of the sleeve 30. This offset distance may enable the light to diffuse outward to provide substantially full coverage over a portion of the length of the sleeve along the inside surface of the sleeve. Substantial full coverage means that light is emitted from at least 80% of an extension of the inside surface and preferably at least 90%. The light devices may be configured to produce an emitted light that overlaps with another adjacent light device along the length of the sleeve and/or around the circumference of the sleeve. As shown in FIG. 1, the emitted light 82 is overlapping along the inside surface 34 from lights configured along the length of the sleeve, or along a length axis 36. Also, as shown in FIG. 2, the light devices 80, 80' configured around the circumference of the sleeve are configured to produce overlapping emitted light 82 along the circumference of the inside surface 34. This combination of overlapping emitted light along the length axis and along the circumferences provides substantially full coverage of a portion of the sleeve, not including the insertion opening 35 and the extended end 37. A reflective material 65 is configured along the inside surface 34 of the outer shell 32. The reflective material may reflect emitted light 82 from the light devices 80 back toward the hollow channel 33.

The sleeve 30 shown in FIG. 8, may have the other features as shown in FIG. 1, including the testicular flange 50, flange lights 58, the vibratory device 75 and the like. FIG. 8 is showing a variation of the cross section of the sleeve.

As shown in FIG. 3, the friction sleeve 40 extends from the outer shell 31 to the inside surface 34 of the sleeve 30. This produces an offset distance 87 from the light device 80' and the inside surface. As described herein, this offset distance may enable the light to diffuse and spread to produce a greater area of coverage on the penis when inserted into the sleeve. The light devices 80 are configured radially outward from the outer shell 31 and emit light through the translucent outer shell. The outside surface 32 is cylindrical and formed by the outer shell 31. A cover layer 39 may be configured radially outside of the outer shell 31 and may be opaque to prevent light from passing through the cover layer. The cover layer may be rigid, such as a rigid plastic and may be detachably attachable to the sleeve 30.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A friction-based therapeutic light penile device comprising:
   a) a sleeve comprising:
      i) an outer shell;
      ii) a friction sleeve configured within the outer shell and forming a hollow channel along an inside surface of the friction sleeve with an insertion opening configured for insertion of a penis;
      iii) a length of the hollow channel from said insertion opening to an extended end; and
      iv) a plurality of light devices configured to emit an emitted light into the hollow channel;
   wherein the plurality of light devices are attached to the outer shell at an offset distance from the hollow channel to produce emitted light producing substantially full coverage over at least 80% of said inside surface along said length of the friction sleeve; and
   wherein the plurality of light devices are configured to produce overlapping emitted light on the inside surface of the sleeve, wherein a first light device of the plurality of light devices emits a first emitted light that overlaps with a second emitted light from a second light device of the plurality of light devices;
   b) a power source to power the light devices;
   wherein the friction sleeve is translucent to allow light to pass through the friction sleeve and into the hollow channel;
   wherein the friction sleeve comprises an elastomeric material that is configured to be deformed by said penis and return to an original shape after being deformed;
   wherein the plurality of light devices are configured circumferentially around the sleeve, wherein the first light device is configured a circumferential offset angle from the second light device.

2. The friction-based therapeutic light penile device of claim 1, wherein the plurality of light devices are configured along a length axis of the sleeve, wherein a first light device is configured more proximal to the insertion opening than a second light device.

3. The friction-based therapeutic light penile device of claim 1, wherein the elastomeric material is selected from the group consisting of silicone, urethane, ethylene propylene rubber, epichlorohydrin, fluorosilicon rubber, and fluoroelastomer.

4. The friction-based therapeutic light penile device of claim 1, wherein the elastomeric material forms an insertion flange forming said insertion opening.

5. The friction-based therapeutic light penile device of claim 4, wherein the insertion flange forms an elongated crease that extended into the insertion opening.

6. The friction-based therapeutic light penile device of claim 1, further comprising a testicular flange that extends from the sleeve and comprises a flange light to emit an emitted light onto the scrotum when the penis is inserted into the hollow channel.

7. The friction-based therapeutic light penile device of claim 6, wherein the testicular flange comprises a flange friction material.

8. The friction-based therapeutic light penile device of claim 1, further comprising an extended end opening configured on an extended end of the sleeve opposite the insertion opening.

9. The friction-based therapeutic light penile device of claim 1, further comprising a reflective material to reflect emitted light back toward the hollow channel.

10. The friction-based therapeutic light penile device of claim 1, further comprising a vibratory device configured to vibrate the friction-based therapeutic light penile device.

11. The friction-based therapeutic light penile device of claim 1, wherein at least a portion of the plurality of light devices produces an emitted light that is a red light having a wavelength from 625 nm to 700 nm.

12. The friction-based therapeutic light penile device of claim 11, wherein at least a portion of the plurality of light devices produces an emitted light that is a blue light having a wavelength from 450 nm to 485 nm.

13. The friction-based therapeutic light penile device of claim 11, wherein at least a portion of the plurality of light devices produces an emitted light that is an infrared light having a wavelength from 700 nm to 1 mm.

14. The friction-based therapeutic light penile device of claim 1, wherein the light device produces a light that heats the inside surface of the friction material to a temperature of more than 90° F.

* * * * *